United States Patent [19]

Baudy et al.

[11] Patent Number: 5,610,164
[45] Date of Patent: Mar. 11, 1997

[54] (THIOPHEN-2-YL)-PIPERIDIN OR TETRAHYDROPYRIDIN AZABICYCLOCARBOXAMIDES

[75] Inventors: Reinhardt B. Baudy, Yardley; James A. Nelson, Washington Crossing, both of Pa.; Mira A. Kanzelberger, Monmouth Junction, N.J.

[73] Assignee: American Home Products Corporation, Madison, N.J.

[21] Appl. No.: 685,132

[22] Filed: Jul. 24, 1996

Related U.S. Application Data

[60] Provisional application No. 60/001,523 Jul. 26, 1995.
[51] Int. Cl.$^6$ ............................ A61K 31/435; C07D 451/02
[52] U.S. Cl. ............................................. 514/304; 546/125
[58] Field of Search ............................. 514/304; 546/125

[56] References Cited

U.S. PATENT DOCUMENTS

| 4,988,814 | 1/1991 | Abou-Gharbia et al. . | |
|---|---|---|---|
| 5,525,600 | 6/1996 | Baudy | 514/212 |
| 5,532,242 | 7/1996 | Cliffe . | |

FOREIGN PATENT DOCUMENTS

WO9311122  6/1993  WIPO .

*Primary Examiner*—Fiona T. Powers
*Attorney, Agent, or Firm*—Arnold S. Milowsky

[57] ABSTRACT

This invention provides compounds having the structure

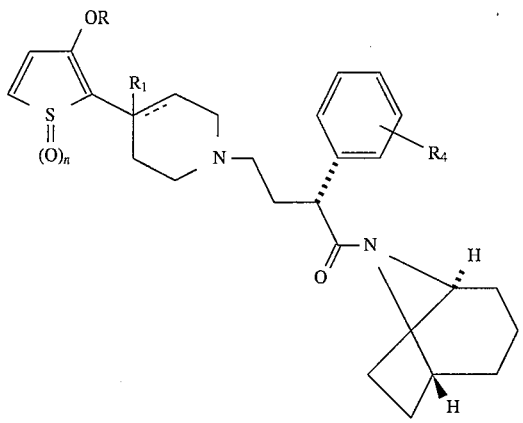

wherein
R is hydrogen, alkyl, alkenyl, alkynyl, —COR$^2$, phenyl, or phenylalkyl; the dotted line represents an optional double bond;
R$^1$ is hydrogen, —OH, OR$^3$, or is absent if the optional double bond is present;
R$^2$ and R$^3$ are each, independently, alkyl, alkenyl, alkynyl, phenyl, or phenylalkyl;
R$^4$ is hydrogen, —OR$^5$, alkyl, alkenyl, alkynyl, —COR$^5$, —CO$_2$R$^5$, —CONR$^5$R$^6$, perhaloalkyl, halogen, phenyl, or phenylalkyl;
R$^5$ and R$^6$ are each, independently, hydrogen, alkyl, alkenyl, alkynyl, phenyl, or phenylalkyl; and
n=0–2
or a pharmaceutically acceptable salt thereof that are useful as antipsychotic, antidepressant and anxiolytic agents useful in the treatment and relief of the symptoms of these disease states.

9 Claims, No Drawings

(THIOPHEN-2-YL)-PIPERIDIN OR TETRAHYDROPYRIDIN AZABICYCLOCARBOXAMIDES

This application claims the benefit of U.S. Provisional application Ser. No. 60/001,523, filed Jul. 26, 1995.

This invention provides compounds having selectivity for the serotonergic 5-HT$_{1A}$ receptor, useful in the treatment of central nervous system disorders, having the structure

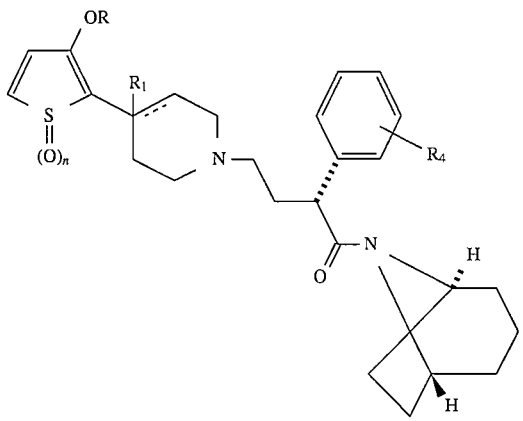

wherein
R is hydrogen, alkyl of 1–6 carbon atoms, alkenyl of 2–7 carbon atoms, alkynyl of 2–7 carbon atoms, —COR$^2$, phenyl, or phenylalkyl of 7–10 carbon atoms;
the dotted line represents an optional double bond;
R$^1$ is hydrogen, —OH, OR$^3$, or is absent if the optional double bond is present;
R$^2$ and R$^3$ are each, independently, alkyl of 1–6 carbon atoms, alkenyl of 2–7 carbon atoms, alkynyl of 2–7 carbon atoms, phenyl, or phenylalkyl of 7–10 carbon atoms;
R$^4$ is hydrogen, —OR$^5$, alkyl of 1–6 carbon atoms, alkenyl of 2–7 carbon atoms, alkynyl of 2–7 carbon atoms, —COR$^5$, —CO$_2$R$^5$, —CONR$^5$R$^6$, perhaloalkyl of 1–6 carbon atoms, halogen, phenyl, or phenylalkyl of 7–10 carbon atoms;
R$^5$ and R$^6$ are each, independently, hydrogen, alkyl of 1–6 carbon atoms, alkenyl of 2–7 carbon atoms, alkynyl of 2–7 carbon atoms, phenyl, or phenylalkyl of 7–10 carbon atoms; and
n=0–2
or a pharmaceutically acceptable salt thereof.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The terms alkyl of 1–6 carbon atoms, alkenyl of 2–7 carbon atoms, and alkynyl of 2–7 carbon atoms, include both straight chain as well as branched carbon chains. In the generic structure described above, when n=0, the sulfur containing ring is a thiophene ring, when n=1, the sulfur containing ring is a thiophene S-oxide, and when n=2, the sulfur containing ring is a thiophene S-dioxide. The term "halogen" refers to fluoro, chloro, bromo, or iodo.

The compounds within the scope of the invention by virtue of their configuration, exhibit stereoisomerism. Such centers can contain either the R or S configuration or can be racemic with respect to such center or centers. Accordingly, the compounds of the invention include the diastereomers, enantiomers, racemates and mixtures thereof.

Of these compounds, the preferred members are those in which n=0; and those in which n=0, and R is alkyl of 1–6 carbon atoms.

The compounds of this invention can be prepared by conventional methods. For example, the appropriately substituted 2-bromo-thiophene can be subjected to a Grignard reaction in which the addition to a 4-piperidone carbamate affords the desired tertiary alcohol. Subsequent hydrolysis of the carbamate yields the desired 4-hydroxy-4-thiophen-2-yl-piperidine as shown in scheme 1.

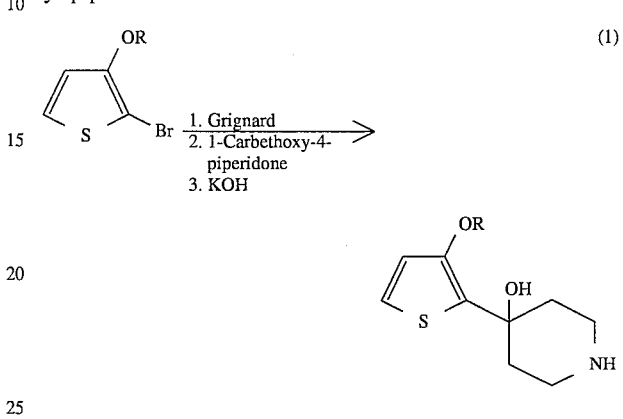

The 4-substituted piperidine is subjected to a reductive amination using the substituted butyraldehyde in the presence of sodium borocyanohydride to yield the final products as illustrated in scheme 2.

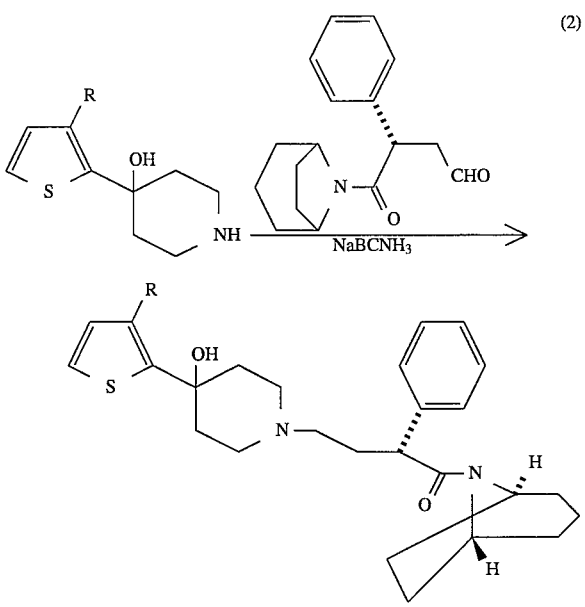

Further functionalization of the piperidine hydroxyl group can be accomplished using standard methodology, and dehydration of the hydroxyl group to provide tetrahydropyridine derivatives can be accomplished under mildly acidic conditions.

Representative compounds of this invention were evaluated and determined to have high affinity for the serotonin 5-HT$_{1A}$ receptor by evaluating the compound's ability to displace [$^3$H]8-OHDPAT (dipropylaminotetralin) from the 5-HT$_{1A}$ serotonin receptor following the procedure of Hall et al., J. Neurochem. 44, 1685 (1985). This standard pharmacological test procedure was employed to analogize this property of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maelen et al., Eur. J. Pharmacol. 1986, 129 (1–2) 133–130). In this standard pharmacological test procedure, buspirone has an IC$_{50}$ of approximately 10 nM.

The results obtained for representative compounds of this invention in the standard pharmacological test procedure described above, are as follows:

| Compound | 5-HT$_{1A}$ Binding (IC$_{50}$) |
| --- | --- |
| Example 1 | 942 nM |
| Example 2 | 0.9 nM |

The results obtained in the standard pharmacological test procedure demonstrate that the compounds this invention possess high affinities for the serotonin 5-HT$_{1A}$ receptor, and consequently, they are useful in the treatment of multi-CNS disorders amenable to treatment with antipsychotic, antidepressant and anxiolytic agents. As such, the compounds of this invention may be administered a mammal in need of antipsychotic, antidepressant and/or anxiolytic medical treatment in an amount sufficient to alleviate the symptoms of the disease state, such as depression, paranoia, schizophrenia, anxiety, sleep disorders, eating disorders, cognitive disorders, panic, social phobia, obsessive compulsive disorders, sexual dysfunction, addiction, and related problems. When administered for the treatment of the above disease states, the compounds of this invention can be administered to a mammal orally, parenterally, intranasally, intrabronchially, transdermally, intravaginally, or rectally.

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carders am used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carders for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers arc useful in sterile liquid form compositions for parenteral administration. The liquid carrier for pressurized compositions can be halogenated hydrocarbon or other pharmaceutically acceptable propellant.

Liquid pharmaceutical compositions which arc sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage to be used in the treatment of a specific psychosis must be subjectively determined by the attending physician. The variables involved include the specific psychosis or state of anxiety or depression and the size, age and response pattern of the patient. Based on the results obtained in the standard pharmacological test procedures, projected oral daily dosages of active compound would be 1–100 mg/kg, preferably between 1–30 mg/kg, and more preferably between 1–10 mg/kg. Projected intravenous daily dosages would be 0.2–20 mg/kg, preferably between 0.2–6 mg/kg, and more preferably between 0.2–2 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the production of representative compounds of this invention.

Preparation of (R)-4-(8-aza-bicyclo[3.2.1.]oct-8-yl)-4-oxo-3-phenylbutyraldehyde The starting (R)-2-phenyl-4-pentenoic acid can be prepared according to the procedure of Cervinka et. al.: Collect. Czech. Chem. Commun. (1967), 32(6), 2295–300.

The reagent nortropane was prepared according to established methods, e.g. J. Org. Chem., (1984), 49, 2081–2.

Under dry nitrogen and protected from light 1-hydroxybenzotriazole (0.46 g, 2.84 mmole) was added to a solution of the starting (R)-2-phenyl-4-pentenoic acid (0.5 g, 2.84 mmole) in methylene chloride (5 mL) at ambient temperature, followed by adding a solution of 1-(3-dimethylaminopropyl)-3-ethylcarbodiimide hydrochloride (0.54 g, 2.84 mmole) in methylene chloride (20 mL). The reaction mixture was stirred for 2 hours after which a solution of nortropane (0.32 g, 2.84 mmole) in methylene chloride (5 mL) was added dropwise and stirring continued at room temperature overnight. The solvent was removed in vacuo at ambient temperature and the residue was partitioned between ethyl acetate (20 mL) and 1N hydrochloric acid (20 mL). The separated organic layer was washed with water (4×20 mL), brine (2×20 mL), dried over magnesium sulfate and filtered. The filtrate was concentrated in vacuo to yield the desired crude (R)-1-(8-aza-bicyclo[3.2.1.]oct-8-yl)-2-phenyl-pent-4-en-1-one which may be purified by flash chromatography on 60 g silica gel using 35% ethyl acetate/hexane as eluant.

The material (0.5 g, 1.86 mmole) was dissolved in a mixture of tetrahydrofuran (13 mL) and water (4 mL) and stirred under nitrogen. Osmium tetroxide (0.37 mL, 0.03 equivalents as a 4% aqueous solution) was added followed by portionwise addition of sodium periodate (1.19 g, 5.56 mmole). After stirring at ambient temperature for 1 hour, water (10 mL), ethyl acetate (20 mL), and brine (10 mL) were added to the reaction mixture. The organic layer was separated, washed with brine (2×20 mL), dried over magnesium sulfate, and filtered. The filtrate was evaporated in vacuo. Column flash chromatography of the residue on 52 g of silica gel with 50% ethyl acetate/hexane as eluant, followed by crystallization from ether/hexane yields 0.29 g of the title compound, m.p. 82°–5° C.

EXAMPLE 1

(R)-1-(8-Aza-bicycl[3.2.1.]oct-8-yl)-4-[4-hydroxy-4-(3-methoxy-thiophen-2-yl)-piperidin-1-yl]-2-phenyl-butan-1-one Hydrochloride Acetic acid (0.48 mL) was added to a solution of the starting 4-hydroxy-4-thiophen-2-yl-piperidine (0.853 g, 4 mmole) and (R)-4-(8-aza-bicyclo[3.2.1.]oct-8-yl)-4-oxo-3-phenyl-butyraldehyde (1.085 g, 4 mmole) in methanol (30 mL) at ambient temperature. Thereafter sodium cyanoborohydride (0.276 g, 4.4 mmole) was added at once and the reaction mixture stirred at room temperature for 3 hours. The mixture was poured into 10% aqueous sodium bicarbonate (60 mL) and extracted with methylene chloride (3×50 mL). The organic extracts were combined, washed with water (50 mL), brine (50 mL), dried over magnesium sulfate and filtered. The filtrate was evaporated in vacuo and the residue dissolved in chloroform (50 mL). Ethanolic hydrochloric acid was added and the resulting solution evaporated. The residue was triturated in ether and the precipitate filtered and dried to yield 1.8 g of the title compound, mp 106°–8° C.
Elemental Analysis for: $C_{27}H_{36}N_2O_3S \cdot HCl$. Calcd: C, 64.20; H, 7.38; N, 5.55. Found: C, 64.08; H, 7.57; N, 5.40.

EXAMPLE 2

(R)-1-(8-Aza-bicyclo[3.2.1.]oct-8-yl)-4-[4-(3-methoxy-thiophen-2-yl)-1,2,3,6-tetrahydro-pyridin-1-yl]-2-phenyl-butan-1-one Hemi-hydrochloride The starting (R)-1-(8-Aza-bicyclo[3.2.1.]oct-8-yl)-4-[4-hydroxy-4-(3-methoxy-thiophen-2-yl)-piperidin-1-yl]-2-phenyl-butan-1-one hydrochloride (example 1, 1.7 g, 3.6 mmole) was dissolved in acetic acid (80 mL) and heated to 140° C. bath temperature for 2½ hours. Thereafter the reaction mixture was stirred at room temperature overnight, evaporated to dryness in vacuo and the residue partitioned between 5% aqueous sodium bicarbonate (50 mL) and chloroform (2×100 mL). The combined organic layer was separated, dried over magnesium sulfate, filtered, and evaporated to dryness in vacuo. Column chromatography on 100 g of silica gel with 3% methanol/chloroform as eluant, followed by crystallization from ethanol/ether with addition of ethanolic hydrochloric acid yields 0.7 g of the title compound, m.p. 100°–3° C.
Elemental Analysis for: $C_{27}H_{34}N_2O_2S \cdot 1.5$ HCl Calcd: C, 64.17; H, 7.08; N, 5.54. Found: C, 64.02; H, 6.94; N, 5.32.

What is claimed is:

1. A compound having the structure

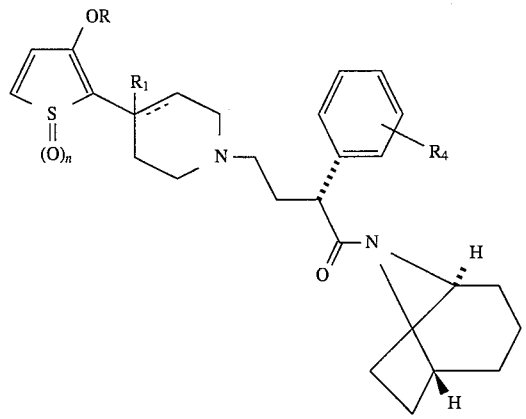

wherein

R is hydrogen, alkyl of 1–6 carbon atoms, alkenyl of 2–7 carbon atoms, alkynyl of 2–7 carbon atoms, —$COR^2$, phenyl, or phenylalkyl of 7–10 carbon atoms; the dotted line represents an optional double bond;

$R^1$ is hydrogen, —OH, $OR^3$, or is absent if the optional double bond is present;

$R^2$ and $R^3$ are each, independently, alkyl of 1–6 carbon atoms, alkenyl of 2–7 carbon atoms, alkynyl of 2–7 carbon atoms, phenyl, or phenylalkyl of 7–10 carbon atoms;

$R^4$ is hydrogen, —$OR^5$, alkyl of 1–6 carbon atoms, alkenyl of 2–7 carbon atoms, alkynyl of 2–7 carbon atoms, —$COR^5$, —$CO_2R^5$, —$CONR^5R^6$, perhaloalkyl of 1–6 carbon atoms, halogen, phenyl, or phenylalkyl of 7–10 carbon atoms;

$R^5$ and $R^6$ are each, independently, hydrogen, alkyl of 1–6 carbon atoms, alkenyl of 2–7 carbon atoms, alkynyl of 2–7 carbon atoms, phenyl, or phenylalkyl of 7–10 carbon atoms; and n=0–2 or a pharmaceutically acceptable salt thereof.

2. The compound of claim 1, wherein n=0 or a pharmaceutically acceptable salt thereof.

3. The compound of claim 2, wherein R is alkyl of 1–6 carbon atoms or a pharmaceutically acceptable salt thereof.

4. The compound of claim 1 which is (R)-1-(8-aza-bicyclo[3.2.1.]oct-8-yl)-4-[4-hydroxy-4-(3-methoxy-thiophen-2-yl)-piperidin-1-yl]-2-phenyl-butan-1-one or a pharmaceutically acceptable salt thereof.

5. The compound of claim 1 which is (R)-1-(8-Aza-bicyclo[3.2.1.]oct-8-yl)-4-[4-hydroxy-4-(3-methoxy-thiophen-2-yl)-piperidin-1-yl]-2-phenyl-butanol-one hydrochloride salt.

6. The compound of claim 1 which is (R)-1-(8-Aza-bicyclo[3.2.1.]oct-8-yl)-4-[4-(3-methoxy-thiophen-2-yl)-1,2,3,6-tetrahydro-pyridin-1-yl]-2-phenyl-butan-1-one or a pharmaceutically acceptable salt thereof.

7. The compound of claim 1 which is (R)-1-(8-Aza-bicyclo[3.2.1.]oct-8-yl)-4-[4-(3-methoxy-thiophen-2-yl)-1,2,3,6-tetrahydro-pyridin-1-yl]-2-phenyl-butan-1-one hemi-hydrochloride.

8. A method of treating anxiety, psychosis, or depression in a mammal in need thereof which comprises administering to said mammal, an effective amount of a compound of the structure

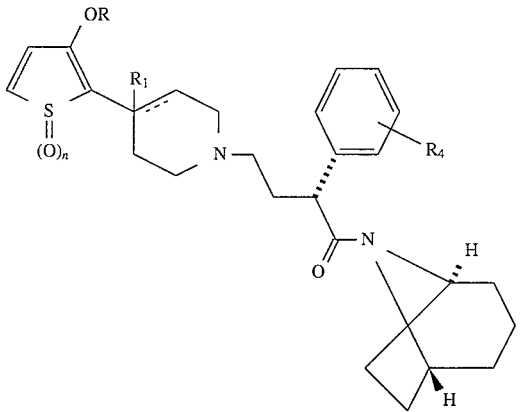

wherein

R is hydrogen, alkyl of 1–6 carbon atoms, alkenyl of 2–7 carbon atoms, alkynyl of 2–7 carbon atoms, —COR$^2$, phenyl, or phenylalkyl of 7–10 carbon atoms;

the dotted line represents an optional double bond;

R$^1$ is hydrogen, —OH, OR$^3$, or is absent if the optional double bond is present;

R$^2$ and R$^3$ are each, independently, alkyl of 1–6 carbon atoms, alkenyl of 2–7 carbon atoms, alkynyl of 2–7 carbon atoms, phenyl, or phenylalkyl of 7–10 carbon atoms;

R$^4$ is hydrogen, —OR$^5$, alkyl of 1–6 carbon atoms, alkenyl of 2–7 carbon atoms, alkynyl of 2–7 carbon atoms, —COR$^5$, —CO$_2$R$^5$, —CONR$^5$R$^6$, perhaloalkyl of 1–6 carbon atoms, halogen, phenyl, or phenylalkyl of 7–10 carbon atoms;

R$^5$ and R$^6$ are each, independently, hydrogen, alkyl of 1–6 carbon atoms, alkenyl of 2–7 carbon atoms, alkynyl of 2–7 carbon atoms, phenyl, or phenylalkyl of 7–10 carbon atoms; and n=0–2 or a pharmaceutically acceptable salt thereof.

9. A pharmaceutical composition which comprises a compound of the structure

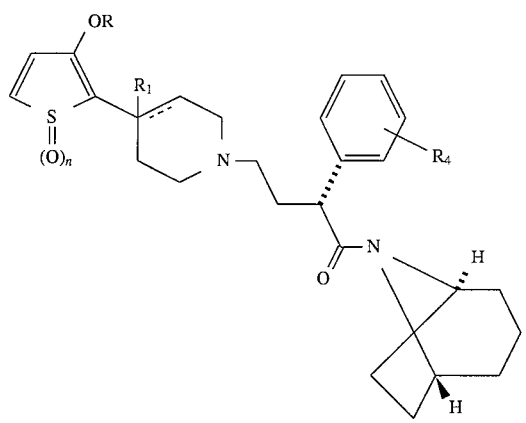

wherein

R is hydrogen, alkyl of 1–6 carbon atoms, alkenyl of 2–7 carbon atoms, alkynyl of 2–7 carbon atoms, —COR$^2$, phenyl, or phenylalkyl of 7–10 carbon atoms;

the dotted line represents an optional double bond;

R$^1$ is hydrogen, —OH, OR$^3$, or is absent if the optional double bond is present;

R$^2$ and R$^3$ are each, independently, alkyl of 1–6 carbon atoms, alkenyl of 2–7 carbon atoms, alkynyl of 2–7 carbon atoms, phenyl, or phenylalkyl of 7–10 carbon atoms;

R$^4$ is hydrogen, —OR$^5$, alkyl of 1–6 carbon atoms, alkenyl of 2–7 carbon atoms, alkynyl of 2–7 carbon atoms, —COR$^5$, —CO$_2$R$^5$, —CONR$^5$R$^6$, perhaloalkyl of 1–6 carbon atoms, halogen, phenyl, or phenylalkyl of 7–10 carbon atoms;

R$^5$ and R$^6$ are each, independently, hydrogen, alkyl of 1–6 carbon atoms, alkenyl of 2–7 carbon atoms, alkynyl of 2–7 carbon atoms, phenyl, or phenylalkyl of 7–10 carbon atoms; and n=0–2 or a pharmaceutically acceptable salt thereof, and a pharmaceutical carrier.

* * * * *